US006417378B1

(12) United States Patent
Hancu

(10) Patent No.: US 6,417,378 B1
(45) Date of Patent: Jul. 9, 2002

(54) DIRECT EPOXIDATION PROCESS USING PRE-TREATED TITANIUM ZEOLITE

(75) Inventor: Dan Hancu, Secane, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/973,663

(22) Filed: Oct. 9, 2001

(51) Int. Cl.⁷ .............................................. C07D 301/06
(52) U.S. Cl. ........................ 549/533; 549/531; 549/532
(58) Field of Search ................................ 549/533, 532, 549/531

(56) References Cited

U.S. PATENT DOCUMENTS 3,351,635 A    11/1967  Kollar ..................... 260/348.5
4,367,342 A    1/1983   Wulff et al. ................. 549/529
4,833,260 A    5/1989   Neri et al. ................... 549/531
5,859,265 A    1/1999   Muller et al. ............... 549/531

FOREIGN PATENT DOCUMENTS

JP         4-352771       12/1992

*Primary Examiner*—Ba K. Trinh
(74) *Attorney, Agent, or Firm*—Kevin M. Carroll

(57) ABSTRACT

The invention is a process for epoxidizing an olefin with hydrogen and oxygen in the presence of a catalyst comprising a noble metal and pretreated titanium zeolite. Titanium zeolite pretreatment comprises contacting the titanium zeolite with a leaching agent prior to use in epoxidation. Surprisingly, the process using the pretreated titanium zeolite shows decreased ring-opening to unwanted glycols and glycol ethers.

15 Claims, No Drawings

DIRECT EPOXIDATION PROCESS USING PRE-TREATED TITANIUM ZEOLITE

FIELD OF THE INVENTION

This invention relates to an epoxidation process using a pre-treated titanium zeolite. The process comprises reacting olefin, hydrogen, and oxygen in the presence of a catalyst comprising a noble metal and a pre-treated titanium zeolite. The zeolite pre-treatment consists of contacting the zeolite with a leaching agent. Surprisingly, the pretreated titanium zeolite shows decreased ring-opening to unwanted glycols and glycol ethers in olefin epoxidation.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For example, JP 4-352771 discloses the epoxidation of propylene oxide from the reaction of propylene, oxygen, and hydrogen using a catalyst containing a Group VIII metal such as palladium on a crystalline titanosilicate. U.S. Pat. No. 5,859,265 discloses a catalyst in which a platinum metal, selected from Ru, Rh, Pd, Os, Ir and Pt, is supported on a titanium or vanadium silicalite. Additionally, it is disclosed that the catalyst may also contain additional elements, including Fe, Co, Ni, Re, Ag, or Au.

One disadvantage of the described direct epoxidation catalysts is that they are prone to ring-open the epoxide product under standard reaction conditions to form less desirable ring-opened by-products such as glycols or glycol ethers. As with any chemical process, it is desirable to develop new direct epoxidation methods and catalysts.

In sum, new processes for the direct epoxidation of olefins are needed. Especially desirable are catalysts that reduce the likelihood of ring-opening of epoxides to glycols or glycol ethers. I have discovered an effective, convenient epoxidation process that reduces unwanted ring-opened products and gives good productivity and selectivity to epoxide.

SUMMARY OF THE INVENTION

The invention is an olefin epoxidation process that comprises reacting olefin, oxygen, and hydrogen in the presence of a catalyst comprising a noble metal and pre-treated titanium zeolite, wherein the pre-treated titanium zeolite is formed by contacting a titanium zeolite with a leaching agent such that greater than 0.1 weight percent of the titanium is removed from the titanium zeolite. I surprisingly found that catalysts produced with the pretreated titanium zeolite give significantly reduced ring-opened by-products compared to untreated titanium zeolite.

DETAILED DESCRIPTION OF THE INVENTION

The process of the invention employs a catalyst that comprises a noble metal and pre-treated titanium zeolite. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

Titanium zeolites may also contain impurities of anatase. Although anatase amounts of less than 5 weight percent anatase (compared to the total amount of titanium zeolite) are acceptable, it is preferred that the titanium zeolite is substantially anatase-free.

The pre-treated titanium zeolite is formed by contacting a titanium zeolite with a leaching agent. The leaching agent can be any compound that is capable of removing greater than 0.1 percent of titanium from the titanium zeolite, based on the amount of titanium in the zeolite (i.e., (moles Ti leached)/(moles Ti in zeolite$_{initial}$)>0.1%). Preferred leaching agents include chelating organic compounds such as glycols, carboxylic acid compounds, and hydroxy ketone compounds. Preferred leaching agents also include mineral acids.

Glycols are organic compounds that contain two or more hydroxy functionalities. Suitable glycols include, but are not limited to, glycerol, propylene glycol, ethylene glycol, and the like. Carboxylic acid compounds contain one or more carboxylic acid functionality. Examples of carboxylic acid compounds include, but are not limited to, acetic acid, pyruvic acid, lactic acid, and the like. Hydroxy ketone compounds contain one or more hydroxy functionality and one or more ketone functionality. Examples of hydroxy ketone compounds include, but are not limited to, acetol, 2-hydroxyacetophene, 2'-hydroxyacetophenone, and the like. Suitable mineral acids include sulfuric acid, hydrochloric acid, phosphoric acid, nitric acid, and the like. Particularly preferred chelating organic compounds include propylene glycol and lactic acid. The leaching agent may also consist of a combination of hydrogen peroxide and a chelating organic compound.

The titanium zeolite pre-treatment can be performed at room temperature, however elevated temperatures greater than 40° C. are preferred. The amount of time required for pre-treatment is not critical, but will depend upon the leaching agent that is employed. Typically, pre-treatment requires greater than 0.5 hour and preferably greater than 10 hours.

The catalyst employed in the process of the invention also contains a noble metal. While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. The manner in which the noble metal is incorporated into the catalyst is not considered to be particularly critical. For example, the noble metal may be supported on the pre-treated zeolite by impregnation means or the like or first supported on another substance such as silica, alumina, activated carbon or the like and then physically mixed with the pre-treated zeolite. Alternatively, the noble metal can be incorporated into the pre-treated zeolite by ion-exchange with, for example, Pd tetraammine chloride with or without added ammonium hydroxide.

There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals. Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the pre-treated zeolite may be fully or partially pre-reduced. Satisfactory catalytic performance can, however, be attained without any pre-reduction. To achieve the active state of palladium, the catalyst may undergo pretreatment such as thermal treatment in nitrogen, vacuum, hydrogen or air.

After noble metal incorporation, the catalyst is recovered. Suitable catalyst recovery methods include filtration and washing, rotary evaporation and the like. The catalyst is typically dried at a temperature greater than about 50° C. prior to use in epoxidation. The drying temperature is preferably from about 50° C. to about 300° C. The catalyst may additionally comprise a binder or the like and may be molded, spray dried, shaped or extruded into any desired form prior to use in epoxidation.

The epoxidation process of the invention comprises contacting an olefin, oxygen, and hydrogen in the presence of a catalyst comprising a noble metal and pre-treated titanium zeolite. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Epoxidation according to the invention is carried out at a temperature effective to achieve the desired olefin epoxidation, preferably at temperatures in the range of 0–250° C., more preferably, 20–100° C. The molar ratio of hydrogen to oxygen can usually be varied in the range of $H_2$:$O_2$=1:10 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin feed ratio of from 0.0001 to 0.1 hour. The time required for the epoxidation may be determined on the basis of the gas hourly space velocity, i.e., the total volume of olefin, hydrogen, oxygen and carrier gas(es) per unit hour per unit of catalyst volume (abbreviated GHSV). A GHSV in the range of 10 to 10,000 $hr^{-1}$ is typically satisfactory.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid phase, it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water.

The following examples merely illustrate the invention. Those skilled in the art will recognize many variations that are within the spirit of the invention and scope of the claims.

EXAMPLE 1

Titanium Leaching Experiments Using Various Leaching Agents

TS-1 can be made according to any known literature procedure. See, for example,. U.S. Pat. No. 4,410,501, DiRenzo, et. al., *Microporous Materials* (1997), Vol. 10, 283, or Edler, et. al., *J. Chem. Soc., Chem. Comm.* (1995), 155.

Runs 1A–1G TS-1 (0.35 g), a hydrogen peroxide solution (50 g, 5 wt. % hydrogen peroxide; 84 wt. % MeOH; 11 wt. % water), and a leaching compound (approximately 2 g) are charged to a one-necked flask equipped with a condenser. The slurry is stirred for 28 hours at 45° C., then filtered under pressurized nitrogen, and dried in a vacuum oven at 45° C. overnight. The filtrate is additionally filtered through a 0.2 µm PTFE membrane, and analyzed for titanium content. Table 1 shows the effect of the combination of $H_2O_2$ and various leaching agents on titanium leaching.

Run 1H

Run 1H is run according to the procedure of 1A–1G, except that only 0.57 g of lactic acid (85 weight percent lactic acid in water solution) is used as the leaching agent.

Run 1J

Run 1J is run according to the procedure of 1A–1G, except that lactic acid (2.0 g, of a 85 weight percent lactic acid in water solution) is used as the leaching agent, and methanol (50 g) is used in place of the hydrogen peroxide solution.

EXAMPLE 2

Catalyst Preparation

Catalyst 2A

TS-1 (1.75 g), a hydrogen peroxide solution (103 g, 12.5 wt. % hydrogen peroxide in water), and propylene glycol (12.03 g) are charged to a one-necked flask equipped with a condenser. The slurry is stirred for 128 hours at 45° C., then filtered under pressurized nitrogen, and dried in a vacuum oven at 45° C. overnight. The filtrate is additionally filtered through a 0.2 µm PTFE membrane, and analyzed for titanium content. Titanium loss is measured at 2.9%.

The pre-treated TS-1 is calcined in air at 550° C. for 4 hours. The pre-treated TS-1 (0.76 g), [Pd(NH$_3$)$_4$](NO$_3$)$_2$ (0.09 g of a 5 weight percent Pd solution in water), and deionized water (10 g) are placed in a 250-mL single-neck round-bottom flask forming a pale white mixture. The flask is connected to a 15-inch cold water condenser and then blanketed with nitrogen at a 150 cc/min flow rate. The flask is inserted into an oil bath at 80° C. and the reaction slurry is stirred. After stirring for 24 hours, the slurry is filtered under pressurized N$_2$, and then the solid is dried in a vacuum oven at 60° C. overnight. The solid catalyst is then calcined in 4% oxygen (remainder nitrogen) at 110° C. for 2 hours and at 150° C. for 4 hours. Measured Pd loading of the catalyst is 0.50 wt. %.

Catalyst 2B

TS-1 (2.2 g), a hydrogen peroxide solution (175 g, 5 wt. % hydrogen peroxide; 84 wt. % MeOH; 11 wt. % water), and lactic acid (7 g, of a 85 weight percent lactic acid in water solution) are charged to a one-necked flask equipped with a condenser. The slurry is stirred for 28 hours at 45° C., then filtered under pressurized nitrogen, and dried in a vacuum oven at 45° C. overnight. The filtrate is additionally filtered through a 0.2 µm PTFE membrane, and analyzed for titanium content. Titanium loss is measured at 5.6%.

Pd incorporation is conducted according to the same procedure as for Catalyst 2A. Measured Pd loading of the catalyst is 0.45 wt. %.

Comparative Catalyst 2C

Pd is incorporated into untreated TS-1 according to the same procedure as for Catalyst 2A. Measured Pd loading of the catalyst is 0.62 wt. %.

EXAMPLE 3

Propylene Epoxidation Studies

To evaluate the performance of the catalysts prepared in Example 2, the epoxidation of propylene using oxygen and hydrogen is carried out. The following procedure is employed.

The catalyst is slurried into 100 grams of methanol/water mixture (75 wt. % MeOH; 25 wt. % H20) and added to the reactor system, consisting of a 300-mL high-pressure reactor and a 1000-mL methanol saturator. The slurry is then heated to 60° C. and stirred at 1500 rpm. A gaseous feed consisting of 10% propylene, 4% oxygen, 4% hydrogen and 82% nitrogen is added to the system with a total flow of 1200 cc/min and a reactor pressure of 300 psi. Both the gas and liquid phase samples are collected and analyzed by G. C.

The epoxidation results, in Table 2, show that the use of a pre-treated TS-1 leads to an unexpected decrease in the amount of ring-opened by-products as shown by increased PO/POE ratio. "POE" means PO equivalents which include propylene oxide (PO), propylene glycol (PG), dipropylene glycol (DPG), 1-methoxy-2-propanol (PM-1), 2-methoxy-1-propanol (PM-2), and acetol.

TABLE 1

Effect of Leaching Agent on Titanium Leaching.

| Pre-Treated Zeolite # | Chelating Organic Compound | Wt. % Chelating Organic | Wt. % $H_2O_2$ | % Ti Loss[a] |
|---|---|---|---|---|
| 1A | PM-1 | 3.84 | 5.1 | 0.016 |
| 1B | Glycerol | 3.84 | 5.1 | 0.25 |
| 1C | PG | 3.84 | 5.1 | 0.36 |
| 1D | Acetic Acid | 3.84 | 5.1 | 1.82 |
| 1E | Acetol | 3.84 | 5.1 | 2.13 |
| 1F | Pyruvic Acid | 3.84 | 5.1 | 2.37 |
| 1G | Lactic Acid | 3.3 | 5.1 | 4.25 |
| 1H | Lactic Acid | 0.94 | 5.1 | 3.11 |
| 1J | Lactic Acid | 3.3 | 0 | 2.09 |

[a]Ti loss = (amount Ti filtrate)/(amount Ti zeolite$_{initial}$)*100

TABLE 2

Propylene Epoxidation Results.

| Catalyst | Amount Catalyst (g) | Run time (h) | Mean PO Productivity (g PO/g cat/h) | Mean POE[a] Productivity (g POE/g cat/h) | PO/POE (%) |
|---|---|---|---|---|---|
| 2A | 0.375 | 45 | 0.2 | 0.26 | 78 |
| 2B | 0.5 | 37 | 0.31 | 0.48 | 68 |
| 2C* | 0.5 | 42 | 0.362 | 0.615 | 58 |

*Comparative Example
[a]POE = PO + ring-opened by-products (PG, DPG, PM-1, PM-2, and acetol).

I claim:

1. A process for producing an epoxide comprising reacting an olefin, oxygen, and hydrogen in the presence of a catalyst comprising a noble metal and pre-treated titanium zeolite, wherein the pre-treated titanium zeolite is formed by contacting a titanium zeolite with a leaching agent such that greater than 0.1 percent of the titanium is removed from the titanium zeolite.

2. The process of claim 1 wherein the leaching agent is a combination of hydrogen peroxide and a chelating organic compound.

3. The process of claim 2 wherein the chelating organic compound is selected from the group consisting of glycols, carboxylic acid compounds, and hydroxy ketone compounds.

4. The process of claim 1 wherein the leaching agent is selected from the group consisting of chelating organic compounds and mineral acids.

5. The process of claim 4 wherein the chelating organic compound is selected from the group consisting of glycols, carboxylic acid compounds, and hydroxy ketone compounds.

6. The process of claim 1 wherein the titanium zeolite is titanium silicalite.

7. The process of claim 1 wherein the titanium zeolite is TS-1.

8. The process of claim 1 wherein the catalyst is comprised of from 0.01 to 5 weight percent noble metal.

9. The process of claim 1 wherein the noble metal is palladium.

10. The process of claim 1 wherein the olefin is a $C_2$–$C_6$ olefin.

11. The process of claim 1 wherein the olefin is propylene.

12. The process of claim 1 further comprising a solvent selected from the group consisting of methanol, ethanol, isopropanol, and tert-butanol, and water.

13. The process of claim 1 further comprising a carrier gas.

14. The process of claim 13 wherein the carrier gas is selected from the group consisting of helium, neon, argon, nitrogen, carbon dioxide, and $C_{1-8}$ saturated hydrocarbons.

15. The process of claim 13 wherein the carrier gas is propane.

* * * * *